United States Patent [19]

Patti et al.

[11] Patent Number: 5,348,731
[45] Date of Patent: Sep. 20, 1994

[54] AEROSOL SPRAY STEEL CAN DISPENSERS WITH CORROSION INHIBITORS

[75] Inventors: Anthony L. Patti, Trumbull; Susan K. Hentrich, Fairfield; Joseph R. Faryniarz, Oxford, all of Conn.

[73] Assignee: Chesebrough-Pond's USA Co., Division of Conopco, Inc., Greenwich, Conn.

[21] Appl. No.: 64,612

[22] Filed: May 19, 1993

[51] Int. Cl.$^5$ .......................... A61K 7/11; A61K 9/12
[52] U.S. Cl. ........................................ 424/47; 424/45; 424/DIG. 1; 424/DIG. 2; 424/71; 424/78.02; 514/957; 252/305
[58] Field of Search ............. 424/47, 45, DIG. 1, 424/DIG. 2, 71, 78.02; 252/305; 514/957

[56] References Cited

U.S. PATENT DOCUMENTS

| | | | |
|---|---|---|---|
| 4,263,275 | 4/1981 | Nandagiri | 424/70 |
| 4,584,021 | 4/1986 | Bartlett | 252/394 |
| 4,604,226 | 8/1986 | Bartlett | 252/392 |
| 5,030,385 | 7/1991 | Bartlett | 252/392 |
| 5,032,317 | 7/1991 | Bartlett | 252/392 |
| 5,164,177 | 11/1992 | Bhatt et al. | 424/47 |

OTHER PUBLICATIONS

Cosmetics & Toiletries, vol. 106, pp. 29–34 (1991).
CA 116(20): 197011x (1991).
"Corrosion Inhibition of Aqueous-Based Aerosol Hair Sprays by Montfort A. Johnson, Spray Technology & Marketing", Jun. 1992.
"Investigation of Low VOC Hair Spray Alternatives" by Martino et al., Spray Technology & Marketing, Mar. 1992.

*Primary Examiner*—Thurman K. Page
*Assistant Examiner*—Raj Bawa
*Attorney, Agent, or Firm*—Milton L. Honig

[57] ABSTRACT

An aerosol composition packaged in a steel can is described. The composition includes water, a propellant and as a corrosion inhibitor, a small amount of ammonium benzoate. The corrosion inhibitor can further be supplemented with ammonium hydroxide.

12 Claims, No Drawings

AEROSOL SPRAY STEEL CAN DISPENSERS WITH CORROSION INHIBITORS

BACKGROUND OF THE INVENTION

Field of the Invention

The invention concerns inhibition of corrosion in steel cans fitted to dispense consumer product aerosols.

The Related Art

Aerosol spray cans are widely used as delivery systems for consumer products. Illustrative of such products are deodorants, antiperspirants, hair colorants, hairsprays, hair styling/conditioning mousses, pot and pan cleaners, room fresheners, furniture polishes, lubricants, hard surface cleaners, animal care sprays, and insecticides. Corrosion is not a problem for aerosol dispensers formed of glass, aluminum, plastic or even certain types of treated steel. Unfortunately, these materials are not as economical as ordinary tin-plated steel. Some amount of protection against corrosion is afforded by the tin, especially in the absence of any significant amount of water.

Environmental concerns have, however, forced replacement of organic solvent-based sprays, with, at least in part, water systems. Corrosion has, thus, become a significant problem. Not only does the aerosol product become contaminated, but when severe enough, corrosion can ultimately cause leaking of the can.

The problems of corrosion have been identified both in areas of the can that contact the liquid phase and also that contact the vapor phase of the aerosol product. Vapor phase attack on the steel has been ascribed to relatively large amounts of water present alongside the volatile propellant in the vapor space of the container.

Intensive research has particularly been pursued in hairspray technology. Widely employed as an anticorrosive is ammonium hydroxide. A system used in Helene Curtis hairsprays is that of sodium benzoate and cyclohexamine.

U.S. Pat. No. 4,604,226 (Bartlett) discloses an inhibitor system comprising a mixture of an amine neutralized phosphate ester and a volatile amine, the latter selected from cyclohexamine, morpholine and isopropylamine. U.S. Pat. No. 4,584,021 (Bartlett) describes related technology wherein the inhibitor system is a mixture of nitroalkane and an amine neutralized phosphate ester. U.S. Pat. No. 4,263,275 (Nandagid) reports a hydroalcoholic, pressurized hairspray composition wherein the anticorrosion agent is a phosphate salt of a quaternary ammonium compound.

Although the foregoing systems are effective, there still is a need for more efficient and less costly systems.

Accordingly, it is an object of the present invention to provide an improved corrosion inhibitor system for steel cans of the aerosol dispensing variety.

It is a further object of the present invention to provide an improved corrosion inhibitor system for steel cans that is able to passivate areas of the steel in contact both with liquid and vapor phases of a product contained therein.

A still further object of the present invention is to provide a corrosion inihibitor system for metal cans utilized to deliver aqueous or hydroalcoholic hairsprays in aerosol form.

These and other objects of the present invention will become more apparent from the following summary and detailed description.

SUMMARY OF THE INVENTION

Now it has been found that ammonium benzoate provides exceptional corrosion inhibition. Thus, an aerosol composition packaged in a steel can is provided which includes:
  (i) from about 0.01 to about 99% water;
  (ii) from about 1 to about 60% propellant; and
  from about 0.1 to about 5% of a corrosion inhibitor which is ammonium benzoate.

Systems of the present invention are particularly useful with hairspray products. These products are characterized by containing at least one film-forming polymeric resin.

In another aspect of the invention, it has been found that ammonium benzoate can be employed in combination with ammonium hydroxide. The combination delivers more than just an additive effect.

DETAILED DESCRIPTION

According to the invention, there will be utilized ammonium benzoate as a corrosion inhibitor for steel can packages. Amounts of the ammonium benzoate will range from about 0.1 to about 5%, preferably from about 0.5 to about 3%, optimally from about 1 to less than 3% by weight. Compositions of the present invention may contain a further corrosion inhibitor in the form of ammonium hydroxide. Amounts of ammonium hydroxide may range from about 0.1 to about 5%, preferably from about 0.5 to 3%, optimally between about 1 and less than 3% by weight. When both ammonium benzoate and ammonium hydroxide are present, their molar ratio will range from about 10:1 to about 1:10, preferably from about 5:1 to about 1:5, optimally between about 2:1 and 1:2.

Compositions of the present invention will also include water as a solvent carrier for active materials. Water will be present in amounts ranging from about 0.01 to about 99%, preferably from about 5 to about 90%, optimally between about 30 and 60% by weight. Normally, water will be the major if not exclusive solvent. Also present can be $C_1$-$C_4$ alcohols such as methanol, ethanol or isopropanol. Levels of these alcohols may range anywhere from about 1 to about 80%, preferably from about 5 to about 30% by weight.

Propellants suitable for the invention can be any liquefiable gas conventionally employed in aerosol containers. Examples of suitable propellants include dimethyl ether, propane, n-butane, isobutane and halocarbons, used singly or in admixture. Dimethyl ether is preferred because of its water-solubility of up to 35% by weight.

The amount of propellant will be governed by normal factors well-known in the aerosol art. The level of propellant may generally range from about 1 to about 60%, preferably from about 5 to about 45%, optimally about 30% of the total composition.

A variety of active components can be utilized with compositions of the present invention. These actives will depend upon intended use of the composition. Actives may include bacteriostats such as triclosan for deodorants, perspiration inhibitors such as aluminum or Zirconium salts for antiperspirants, film-forming resins for hairsprays, surfactants for cleaners, oils for lubricants, or pesticides for animal care and insecticide products.

Hairsprays are of particular concern with respect to the present invention. Consequently, the following discussion will focus upon hairspray compositions. Film-forming polymeric resins are the key active of a hairspray composition. These resins may either be nonionic, anionic, cationic or amphoteric type hair fixative polymers. They may be vinyl polymerized compounds or condensation polymers.

Examples of anionic hair fixative polymers are the copolymers of vinyl acetate and crotonic add, terpolymers of vinyl acetate, crotonic acid and a vinyl ester of an alpha-branched saturated aliphatic monocarboxylic add such as vinyl neodecanoate; copolymers of methyl vinyl ether and maleic anhydride (molar ratio about 1.1) wherein such copolymers are 50% esterified with a saturated alcohol containing from 1 to 4 carbon atoms such as ethanol or butanol; and acrylic copolymers, terpolymers, etc., containing acrylic acid or methacrylic acid as the anionic radical-containing moiety and esters of acrylic or methacrylic acid with one or more saturated alcohols having from 1 to 22 carbon atoms such as methyl methacrylate, ethyl acrylate, ethyl methacrylate, n-butyl acrylate, t-butyl acrylate, n-butyl acrylate, t-butyl methacrylate, n-butyl methacrylate, n-hexyl acrylate, n-octyl acrylate, lauryl methacrylate and behenyl acrylate. One specific example is the emulsion polymerized terpolymer of methacrylic acid, n-butyl acrylate and ethyl acrylate (e.g., in a weight percent ratio of 31:42:27, respectively). Another specific example is Ultrahold ® (CTFA-Cosmetic, Toiletries and Fragrance Association-designation of Acrylate/Acrylamide Copolymer).

Amphoteric polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair fixative polymer is Amphomer ® sold by the National Starch and Chemical Corporation.

Examples of nonionic hair fixative polymers are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from ISP Corporation such as homopolymers of N-vinylpyrrolidone having an average molecular weight of about 630,000 sold by ISP (formerly GAF Corporation) under the tradename PVP K-90 and those having an average molecular weight of about 1,000,000 sold under the trademark of PVP K-120.

Examples of cationic hair fixative polymers are copolymers of amino-functional acrylate monomers such as lower alkylaminoalkyl acrylate or methacrylate monomers such as dimethylaminoethyl methacrylate with compatible monomers such N-vinylpyrrolidone, vinyl caprolactam, or alkyl methacrylates such as methyl methacrylate and ethyl methacrylate and alkyl acrylates such as ethyl acrylate and n-butyl acrylate. Cationic hair fixative polymers containing N-vinylpyrrolidone are commercially available from ISP Corporation such as those sold under the trademarks of Copolymer 845 and Copolymer 937 (copolymers of N-vinylpyrrolidone and t-butylaminoethyl methacrylate of average molecular weight about 1,000,000) and Gafquat ® 755 and 755N (quaternary ammonium polymers formed by the reaction of dimethyl sulfate and a copolymer of N-vinylpyrrolidone and dimethylaminoethyl methacrylate of average molecular weight about 1,000,000).

Where the film-forming resins are formed through vinyl polymerization, the monomers may best be selected from the group consisting of styrene, acrylic acid and $C_1$-$C_{20}$ esters, methacrylic acid and $C_1$-$C_{20}$ esters, vinyl acetate, crotonic acid and $C_1$-$C_{20}$ esters, vinyl neodecanoate, acrylamide, methacrylamide, maleic add and $C_1$-$C_{20}$ esters, and combinations of these.

With certain of the polymers, it may be necessary to neutralize some acidic groups to promote solubility/dispersibility. Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). Amounts of the neutralizing agents will range from about 0.001 to about 10% by weight.

Small quantities of surfactant ranging anywhere from 0.1 to about 10%, preferably from about 0.1 to about 1%, optimally about 0.3% by weight may be present in the compositions of the invention. The surfactant may be an anionic, nonionic or cationic emulsifier. Particularly preferred are nonionic emulsifiers which are formed from alkoxylation of hydrophobes such as fatty alcohols, fatty acids and phenols. Illustrative of such material is Triton X-100 ®, an isooctyl phenyl polyethoxyethanol.

The present hair treatment compositions may be formulated as sprays in aerosol or nonaerosol forms. If an aerosol hairspray is desired, a propellant must be included in the composition. This agent is responsible for expelling the other materials from the container and forming the hairspray character.

The propellant gas can be any liquefiable gas conventionally used for aerosol containers. Preferably the density of the propellant or mixture thereof is less than the hairspray concentrate so that pure propellant is not emitted from the container. Examples of suitable propellants include dimethyl ether, propane, n-butane and isobutane, used singly or admixed. Dimethyl ether is preferred because of its water-solubility up to 35% by weight.

The amount of the propellant gases is governed by normal factors well known in the aerosol art. For hairsprays the level of propellant is generally from about 3 to about 50%, preferably from about 5 to about 45%, optimally about 30% of the total composition.

Resins when deposited upon hair quite often impart dullness. Counteraction of the dullness effect may be achieved by incorporating low levels of $C_{10}$-$C_{20}$ fatty alcohol esters. Particularly preferred is cetearyl octanoate. Amounts of these luster imparting agents will range from about 0.001 to about 1%, preferably from about 0.01 to about 0.5%, optimally from about 0.02 to about 0.1% by weight.

Compositions of this invention may contain any other ingredient normally used in hairsprays. These other ingredients may include antifoam agents, proteins, antioxidants, fragrances, antimicrobials and sunscreens. Each of these ingredients will be present in an amount effective to accomplish its purpose.

The following Examples will more fully illustrate the embodiments of this invention. All parts, percentages and proportions referred to herein and the appended claims are by weight unless otherwise indicated.

EXAMPLE 1

An aerosol hairspray was prepared according to the following formula and incorporated into a tin-plated steel can.

TABLE I

| Components | Weight % |
| --- | --- |
| SDA Alcohol 40 | 65.00 |
| Propellant A85 (propane/isobutane) | 15.00 |
| Deionized Water | 13.63 |
| Resyn 28-29-30 ® | 5.50 |
| AMP 95 ® | 0.54 |
| Fragrance | 0.13 |
| Ammonium Benzoate | 0.10 |
| Ammonium Hydroxide | 0.10 |

EXAMPLE 2

An aerosol hairspray is prepared according to the following formula and incorporated into a tin-plated steel can.

TABLE II

| Components | Weight % |
| --- | --- |
| SDA Alcohol 40 | 58.97 |
| Dimethyl Ether | 20.00 |
| Deionized Water | 16.00 |
| Amphomer ® | 4.25 |
| AMP 95 ® | 0.78 |
| Ammonium Benzoate | 0.50 |

EXAMPLE 3

An aerosol deodorant is prepared according to the following formula:

TABLE III

| Components | Weight % |
| --- | --- |
| SDA Alcohol 40 | 50.00 |
| Dimethyl Ether | 30.00 |
| Demineralized Water | 20.00 |
| Triclosan | 1.00 |
| Ammonium Benzoate | 1.00 |
| Perfume | 0.50 |

EXAMPLE 4

An aerosol antiperspirant is prepared according to the following formula:

TABLE IV

| Components | Weight % |
| --- | --- |
| Propellant A85 | 70.00 |
| SDA Alcohol 40 | 21.50 |
| Aluminum Zirconium Glyconate | 3.00 |
| Cyclomethicone | 2.00 |
| Ammonium Benzoate | 1.00 |
| Ammonium Hydroxide | 0.50 |
| Perfume | 0.50 |

EXAMPLE 5

An aerosol insecticide is prepared according to the following formula:

TABLE V

| Components | Weight % |
| --- | --- |
| Water | 63.00 |
| Dimethyl Ether | 35.00 |
| Parathion ® | 1.00 |
| Polyoxyethylene (20) Sorbitan Monooleate | 0.50 |
| Ammonium Benzoate | 0.50 |
| Perfume | 0.50 |

The foregoing description and Examples illustrate selected embodiments of the present invention. In light thereof, various modifications will be suggested to one skilled in the art, all of which are within the spirit and purview of this invention.

What is claimed is:

1. An aerosol composition packaged in a steel can comprising:
   (i) from about 0.01 to about 99% water;
   (ii) from about 1 to about 60% propellant; and
   (iii) from about 0.1 to about 5% of a corrosion inhibitor which is a combination of ammonium benzoate and ammonium hydroxide in molar ratio from about 10:1 to about 1:10.

2. A composition according to claim 1 which is a hairspray and further includes from about 0.1 to about 20% by weight of a film-forming polymeric resin.

3. A composition according to claim 2 wherein the film-forming polymeric resin is constituted from a monomer selected from the group consisting of vinylacetate, crotonic acid, vinyl neodecanoate, methyl vinyl ether, acrylic acid and $C_1$-$C_{20}$ esters thereof, methyl methacrylate, ethyl acrylate, ethyl methacrylate, n-butyl acrylate, t-butyl acrylate, acrylamide, methacrylamide, t-butyl amino ethyl methacrylate, N-vinyl pyrrolidone and combinations thereof.

4. A composition according to claim 2 wherein the film-forming polymeric resin is a polyester or polyesteramide.

5. A composition according to claim 2 wherein the film-forming polymeric resin is selected from the group consisting of polyvinylpyrrolidone, polyvinylacetate, octylacrylamide/acrylates/butyl amino ethyl methacrylate copolymer, vinyl acetate/crotonic acid/vinyl neodecanoate, acrylate/acrylamide copolymer, isophthalic acid/sulfoisophthalic acid/diethylene glycol polyester and combinations thereof.

6. A composition according to claim 1 wherein the molar ratio ranges from about 2:1 to about 1:2.

7. A composition according to claim 1 further comprising a $C_1$-$C_4$ alcohol present in an amount from about 1 to about 80% by weight.

8. A composition according to claim 1 further comprising from about 0.001 to about 10% by weight of a neutralizing agent which is an amino alcohol.

9. A composition according to claim 1 wherein the molar ratio is about 1:1.

10. A method for inhibiting corrosion of steel cans that store aerosol compositions comprising from about 0.01 to about 99% water and from about 1 to about 60% propellant, said method comprising adding from about 0.1 to about 5% of a corrosion inhibitor combination of ammonium benzoate and ammonium hydroxide in a molar ratio from about 10:1 to about 1:10.

11. A method according to claim 10 wherein the molar ratio ranges from about 2:1 to about 1:2.

12. A method according to claim 11 wherein the molar ratio is about 1:1.

* * * * *